United States Patent [19]

Jakubczak

[11] Patent Number: 4,651,717

[45] Date of Patent: Mar. 24, 1987

[54] MULTIPLE ENVELOPE TISSUE EXPANDER DEVICE

[75] Inventor: Eugene R. Jakubczak, Bay City, Mich.

[73] Assignee: Dow Corning Corporation, Midland, Mich.

[21] Appl. No.: 719,926

[22] Filed: Apr. 4, 1985

[51] Int. Cl.$^4$ ............................................. A61M 29/02
[52] U.S. Cl. ................................. 128/344; 128/1 R; 623/8
[58] Field of Search ................. 128/1 R, 344; 623/7, 623/8

[56] References Cited

U.S. PATENT DOCUMENTS

| | | | |
|---|---|---|---|
| 3,416,160 | 12/1968 | Arion. | |
| 3,559,214 | 2/1971 | Pangman. | |
| 3,663,968 | 5/1972 | Mohl et al. | 623/7 X |
| 3,681,787 | 8/1972 | Perras | 623/8 |
| 3,852,833 | 12/1974 | Koneke et al. | 623/7 |
| 4,125,117 | 11/1978 | Lee | 623/7 X |
| 4,157,085 | 6/1979 | Austad | 128/1 R |
| 4,190,040 | 2/1980 | Schulte | 128/1 R |
| 4,205,401 | 6/1980 | Frisch. | |
| 4,217,889 | 8/1980 | Radovan et al. | 128/1 R |
| 4,245,644 | 1/1981 | Evans | 623/7 X |
| 4,298,998 | 11/1981 | Naficy | 623/8 |
| 4,428,364 | 1/1984 | Bartolo | 128/1 R |
| 4,433,440 | 2/1984 | Cohen | 623/8 |
| 4,574,780 | 3/1986 | Manders | 128/1 R |

FOREIGN PATENT DOCUMENTS 2199266 3/1974 France.

OTHER PUBLICATIONS

Journal Article—"Augmentation Mammaplasty with the Akiyama Prosthesis", Y. Mutou, *British Journal of Plastic Surgery*, 23, pp. 58–62, 1970.
Data Sheet—"Reconstructive Mammary Implant (Birnbaum Design)" No. 120318, Oct. 1977, McGhan Medical Corporation, Santa Barbara, Calif., 4 pages.
Journal Article—"Customized Reconstruction of the Breast after Radical and Modified Radical Mastectomies", Birnbaum et al., *The Western Journal of Medicine*, pp. 388–390, Nov. 1976.
Data Sheet: "Silastic(R) Percutaneous Skin Expander (Lapin Design)", Dow Corning Wright, Arlington, Tenn., No. L080–0011, 4 pages, 1981.
Data Sheet: "Radovan Subcutaneous Tissue Expander", Heyer-Schulte Corp., Goleta, Calif., No. 101513–001-05-1179, 4 pages.
Data Sheet: "Saline-Fill Skin Expander", Cox-Uphoff, Int'l., Santa Barbara, Calif., 4 pages, Preliminary Data Sheet.
Data Sheet No. 120060–8206, "Saline Fill Skin & Tissue Expander", Cox-Uphoff, Inc., Santa Barbara, Calif., 2 pages.

*Primary Examiner*—Albert J. Makay
*Assistant Examiner*—Steven E. Warner
*Attorney, Agent, or Firm*—Richard E. Rakoczy

[57] ABSTRACT

This invention relates to an implantable, multiple envelope tissue expander and to a method of using the same to produce a flap or section of tissue having a preselected shaped for use in plastic surgical procedures. The device consists essentially of at least two separately inflatable envelopes wherein one is used as a base and is fixed to body members underlying the tissue to be expanded. The other envelope is smaller in volume than the first and is attached to the upper half of the base envelope to expand the tissue overlying the second envelope to a greater extent than is accomplished by the first envelope to thereby produce a section of tissue with a preselected shape.

16 Claims, 7 Drawing Figures

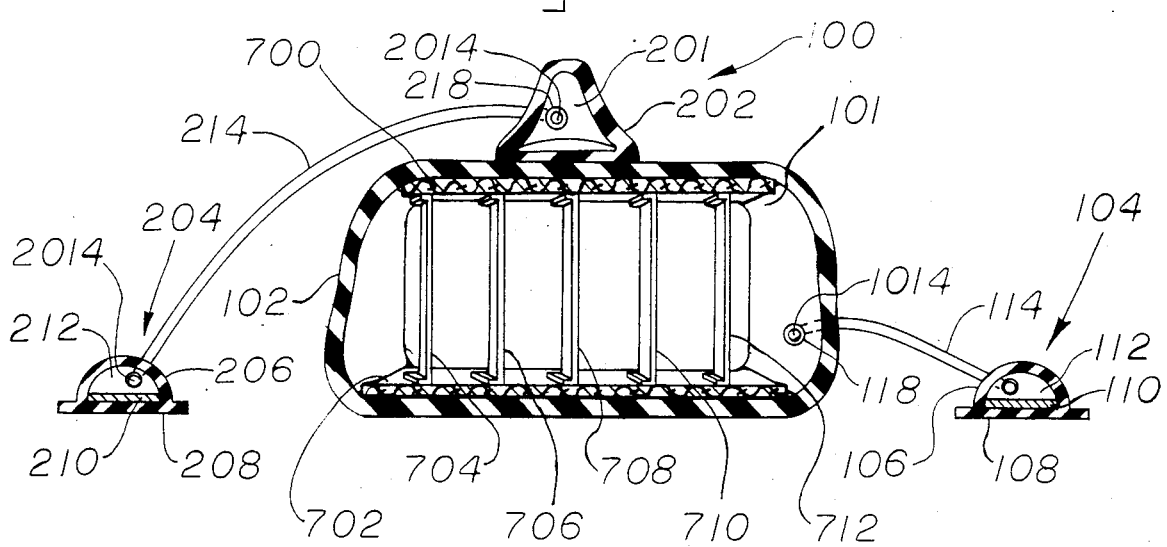

MULTIPLE ENVELOPE TISSUE EXPANDER DEVICE

This invention relates to a device and a method for expanding tissue for use in reconstructive plastic surgery. The novel multiple chamber tissue expander device creates tissue having a preselected shape which is determined by the manner in which the device is secured beneath the tissue to be expanded and the orientation of and the degree to which each separate envelope is inflated.

Subcutaneous tissue expanders have come into wide use because of the variety of plastic surgical procedures that have been developed which either require that tissue be expanded to receive an implant or that a flap of tissue be generated for use on some other part of the body. For example, tissue covering the chest wall after a radical mastectomy may need to be expanded before a subcutaneous mammary prosthesis can be implanted or a flap of tissue may need to be generated to replace scarred tissue on some other part of the body.

Various types of human tissue expanders are commercially available: SILASTIC ® Percutaneous Skin Expander from Dow Corning Wright, Arlington, Tenn. 38002; the RADOVAN TM Subcutaneous Tissue Expander from Heyer-Schulte Corporation, Goleta, Calif. 93017 which is described in U.S. Pat. No. 4,217,889 to Radovan, et al. (issued Aug. 19, 1980) and the CUI Skin Expander from Cox-Uphoff International, Santa Barbara, Calif. 93103. These tissue expanders are implanted and filled percutaneously (usually with an isotonic saline solution) gradually over an extended time period for use in post mastectomy reconstruction techniques to prepare a pocket for the receipt of an implantable mammary prosthesis, for use in the correction of hypoplasia, or to generate additional tissue for use in scar revision procedures. Austad, in U.S. Pat. No. 4,157,085 (issued June 5, 1979) teaches an osmotically expandable tissue expander which does not require percutaneous inflation.

A number of implantable mammary prostheses are known which can be partially or fully inflated after the prosthesis is inserted beneath the skin. For example, see U.S. Pat. No. 3,416,160 to Arion (issued Dec. 17, 1968) and "Augmentation Mammaplasty With the Akiyama Prosthesis" by Y. Mutou in the *British Journal of Plastic Surgery*, volume 23, pages 58–62 (1970) for single envelope, inflatable mammary prostheses. French Pat. No. 2,199,266 (granted Mar. 25, 1974) to Leguen teaches a dual envelope mammary prosthesis wherein one envelope is prefilled before implantation and the other envelope can be filled after implantation. Product data sheet number 120318 dated 10/77 from the McGhan Medical Corporation of Santa Barbara, Calif. entitled "Reconstructive Mammary Implant (Birnbaum Design)" shows a dual envelope mammary prosthesis where one part of the prosthesis has a gel-filled envelope and the other integral envelope along side the first is inflatable with saline after implantation. Use of some of these prostheses is described in a November, 1976, article entitled "Customized Reconstruction of the Breast After Radical and Modified Radical Mastectomies" by Birnbaum, et al, in *The Western Journal of Medicine* on pages 388–390. In U.S. Pat. No. 3,559,214 (issued Oct. 17, 1968), Pangman teaches a multiple envelope mammary prosthesis where the three integral envelopes or chambers (prefilled before implantation) are side by side and are of substantially equal volume to cause the prosthesis to retain a desired (natural) shape despite movement by the patient. Frisch in U.S. patent application Ser. No. 06/674,457 entitled "Shape Retention Tissue Expander and Method of Using" which was filed on Nov. 26, 1984 and is assigned to the same assignee as the present invention teaches a dual envelope skin expander whose purpose is to create a hemispherical pocket beneath the skin.

None of the above devices appear to be specifically intended to produce a flap of tissue wherein one part of the flap is expanded more than the rest to produce a flap which has a very specific shape. The Birnbaum Design Implant might accomplish some directional shaping of the flap if the inflatable/gel combination prosthesis is used since one envelope (the prefilled envelope) of the implant does not expand relative to the other envelope. The Radovan, et al. Patent teaches that the shape of the tissue flap is determined by the shape of the base and use of a stiff base is preferred to restrict the shape of the flexible expanding envelope attached to the base. None of these devices teach a method or device which is specifically designed, for example, to expand the center of a flap of tissue to a greater extent than the surrounding sides of the expanded tissue to produce a flap having a complex shape.

SUMMARY OF THE INVENTION

One object of this invention is to provide a tissue expander device which is capable of producing a flap of tissue of complex shape such as where the center of the flap is expanded to a greater extent than the surrounding tissue overlying the device. This device can be used where an implant of a specific shape is to be inserted under the expanded tissue as well as in surgical procedures where a flap of skin of a particular shape is needed for grafting to another part of the body such as in scar revision or to replace tissue lost by trauma or burns.

Another object of this invention is to provide a method by which a flap of tissue of a preselected shape can be generated. These and other objects are provided by an implantable, multiple envelope tissue expander which consists essentially of at least two separately inflatable envelopes wherein one chamber forms a base and has a means thereon to fix the lower part of the chamber to underlying body members such as muscle to thereby position the device beneath the tissue to be expanded in a preselected orientation. At least one other separately inflatable envelope is affixed to the upper half of the envelope forming the base to enable the tissue overlying the other envelope to be expanded more than that surrounding and overlying the base. The base can be gradually inflated first followed by the other envelope(s) or else all envelopes can be gradually expanded at the same time. The envelopes affixed to the base must be smaller in volume upon inflation than the inflated base to accomplish proper shaping of the tissue flap and preferably, the volume of each envelope affixed to the base is less than 50% of the volume of the base envelope after complete inflation of each envelope. In an alternative embodiment, the lower envelope can contain a shape retaining means such as strips affixed to the upper and lower interior walls of the envelope to cause the lower envelope to inflate to a preselected shape.

BRIEF DESCRIPTION OF THE DRAWINGS

The above and other objects, features and advantages of the present invention will become apparent to those skilled in the art upon an examination of the following description and drawings.

In the drawings:

FIG. 7 is an alternative embodiment of the device of FIG. 1 in cross-section further showing a shape-retaining means placed in the lower envelope.

DETAILED DESCRIPTION OF THE INVENTION

Figure 1:
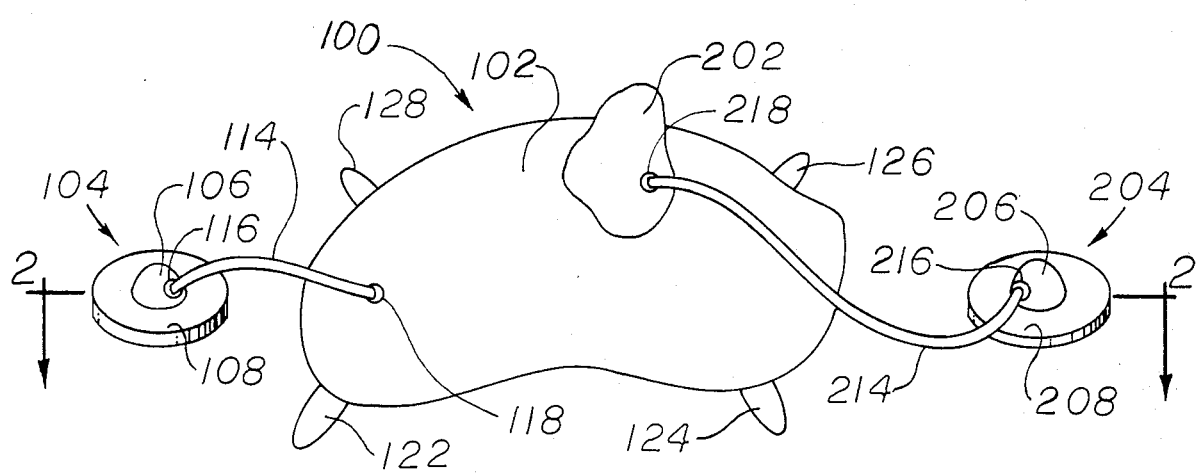
FIG. 1 is a perspective view of one embodiment of the present invention shown as a dual envelope tissue expander which is shown inflated.
Figure 2:
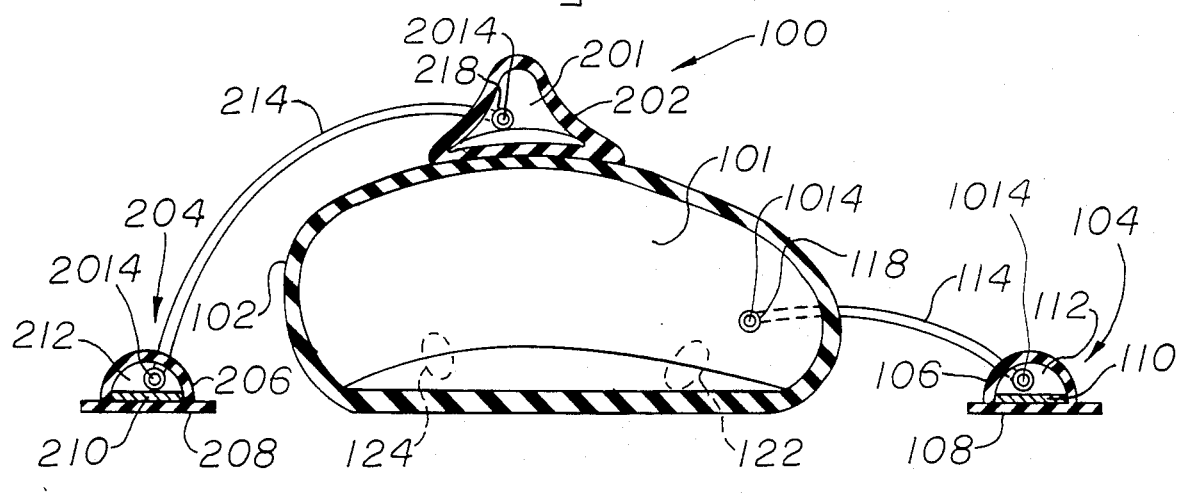
FIG. 2 is a cross-sectional view of FIG. 1 taken along line 2—2.

Referring to the Drawings, FIGS. 1 and 2 depict one embodiment of a multiple envelope tissue expander of the present invention shown as device 100 which consists essentially of envelope 102 which has a generally hemispherical shape after complete inflation and has a means for inflating and thus pressurizing envelope 102. That inflation means is shown in the form of injection button 104 of conventional design having a self-sealing hollow dome 106 of, for example, biocompatible silicone elastomer sealingly mounted to a flat biocompatible silicone elastomer base 108 to permit inflation by addition of a biocompatible fluid such as isotonic saline into the interior region 101 of envelope 102. Button 104 further contains a needlestop 110 of stainless steel or other rigid, biocompatible material.

Figure 3:
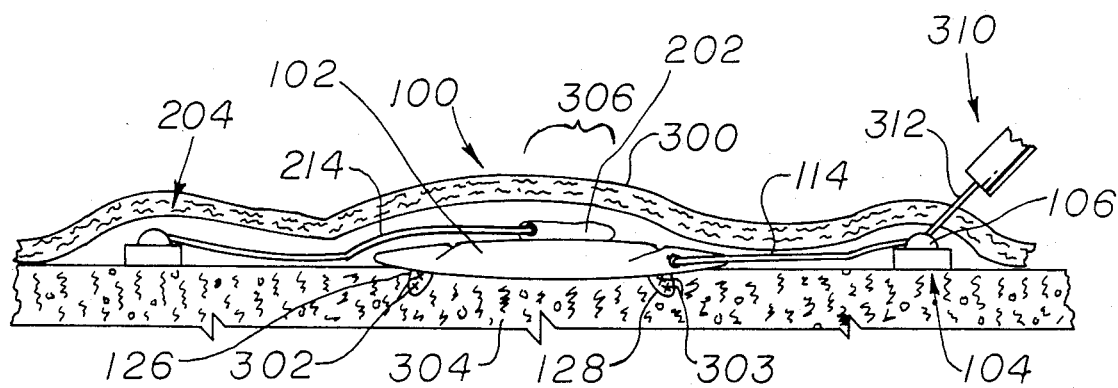
FIG. 3 is a partial sectional side view of an uninflated dual envelope tissue expander implanted beneath the skin.

As shown in FIG. 3, a hypodermic syringe needle 312 is used to introduce biocompatible fluid into the hollow region 112 beneath dome 106. The fluid travels through the center 1014 of tube 114 which can be of a biocompatible silicone elastomer from region 112 into hollow interior region 101 of envelope 102 because the ends of tube 114 are sealed to dome 106 and envelope 102 at attachment points 116 and 118, respectively, with, for example, a medical grade silicone adhesive such that center 1014 is in communication with regions 112 and 101.

Envelope 102 forms a base for device 100 and contains four conventional fixation tabs 122, 124, 126 and 128 which can be strips of polyester fiber mesh reinforced silicone elastomer which are fixed to the lower portion of envelope 102 such as by means of a medical grade silicone adhesive. The tabs are fixed in locations which will enable a surgeon to suture the fixation tabs to body members underlying the tissue to be expanded and to thereby retain envelope 102 in a preselected orientation with respect to the overlying tissue as will be described in connection with FIGS. 3–5. The tabs can also be of a tissue ingrowth material such as a polyester felt to achieve fixation.

The fixation tabs thus define the lower half of envelope 102 and envelope 202 is securely fixed to the upper half of envelope 102 such as by means of a medical grade of silicone adhesive. When envelope 102 is sutured to underlying body members and inflated, envelope 102 forms a base which holds envelope 202 in a fixed position and allows the tissue located over envelope 202 to be expanded (as envelope 202 is inflated) to a greater extent than the tissue expansion caused by the inflation of the base envelope 102. The location of envelope 202 on the upper half of envelope 102 determines the final shape of the resulting flap. If envelope 202 is placed on the lower half of the surface of envelope 102 near the underlying body member, only lateral, even expansion of the tissue will occur and the foregoing objects of the present invention will not be achieved.

After both envelopes are inflated to their intended volumes, the volume of envelope 202 must be less than the volume of envelope 102 to achieve the varying degrees of tissue expansion needed to properly shape the tissue flap being generated. Preferably, the volume of envelope 202 is no greater than 50% of the volume capacity of envelope 102 after complete inflation. To achieve appropriate shaping of the tissue flap, it is contemplated that more than one envelope can be fixed to the upper surface of envelope 102 so that a variety of appropriately shaped tissue flaps can be generated by using the device of the present invention.

The construction of envelope 202 and components affixed thereto are similar to those described for envelope 102. Envelope 202 contains a separate injection button 204 of conventional design having a self-sealing hollow dome 206 sealingly attached to a flat base 208 containing needlestop 210 such that biocompatible fluid injected through dome 206 into hollow region 212 travels through the center 2014 of hollow tube 214 from attachment point 216 to attachment point 218 where the fluid enters hollow region 201 of envelope 202.

Figure 6:
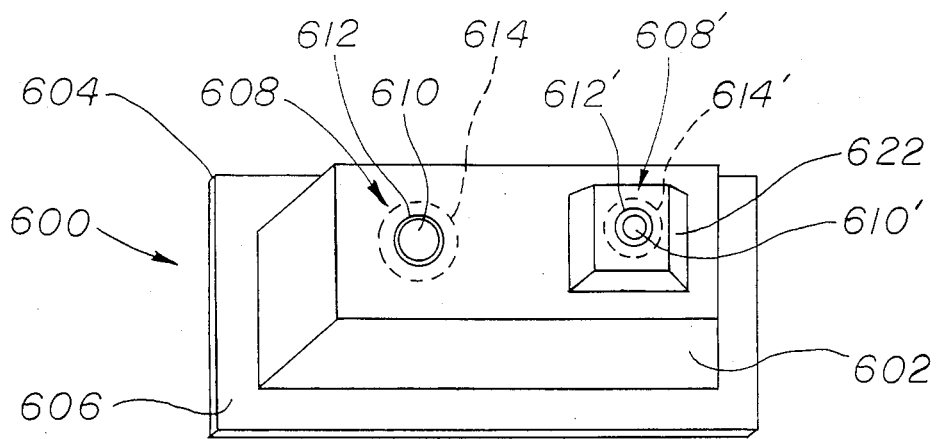
FIG. 6 is a perspective view of an alternative embodiment of the present invention.

One example of an injection button which can be used is found in U.S. Pat. No. 4,190,040 to Schulte (issued Feb. 26, 1980). In alternative embodiments, as shown in FIG. 6, one or both of the above remote inflation means could be mounted directly on the envelope and an injection button of the type described in U.S. Pat. No. 4,428,364 to Bartolo (issued Jan. 31, 1984) could be used and that patent is hereby incorporated by reference to teach such an injection button.

Interior regions 101 and 201 are shown as being inflated, but empty, for the purposes of clarity. The fluid used to inflate envelopes 102 and 202 is preferably an isotonic saline solution although other biocompatible fluids which will remain under pressure within each envelope, such as a silicone gel, can also be used. In another alternative embodiment, the inflation means used to pressurize one or both envelopes could comprise a means for osmotically expanding one or both envelopes over a period of time such as that taught in the aforementioned Austad patent or U.S. Pat. No. 4,138,382 to Polmanteer (issued Feb. 6, 1979).

Envelopes 102 and 202 are preferably constructed of a biocompatible silicone elastomer such as one of the medical grade silicone elastomers commonly used in the manufacture of mammary implants or tissue expanders (e.g., those which are available from Dow Corning Corporation, Midland, Mich. 48686), but could be manufactured of any other biocompatible elastomer material or combination of materials such as a polyurethane material. Envelope 202 is fixed to the desired location on the upper half of envelope 102 by any appropriate means which will hold it on the surface of the upper half of envelope 102, e.g., by a medical grade silicone adhesive.

Figure 4:
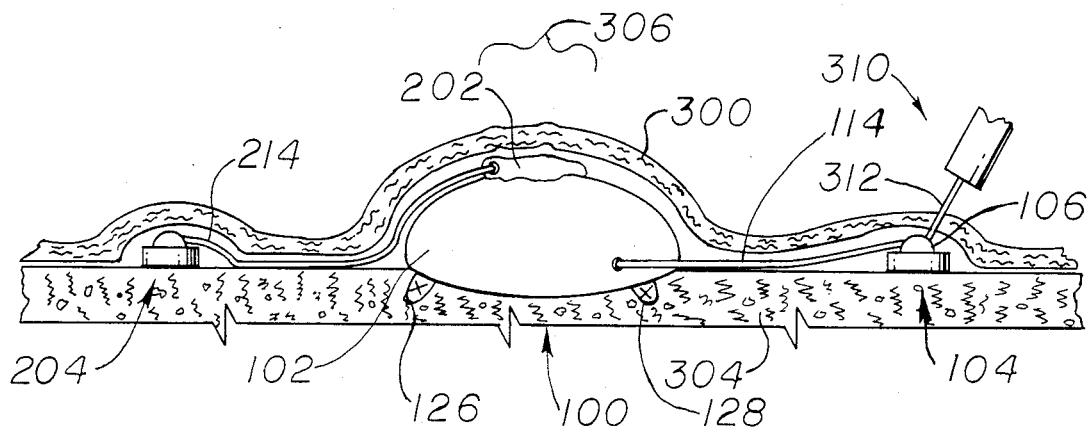
FIG. 4 is a partial sectional side view of a partially uninflated tissue expander showing the base chamber fully inflated.
Figure 5:
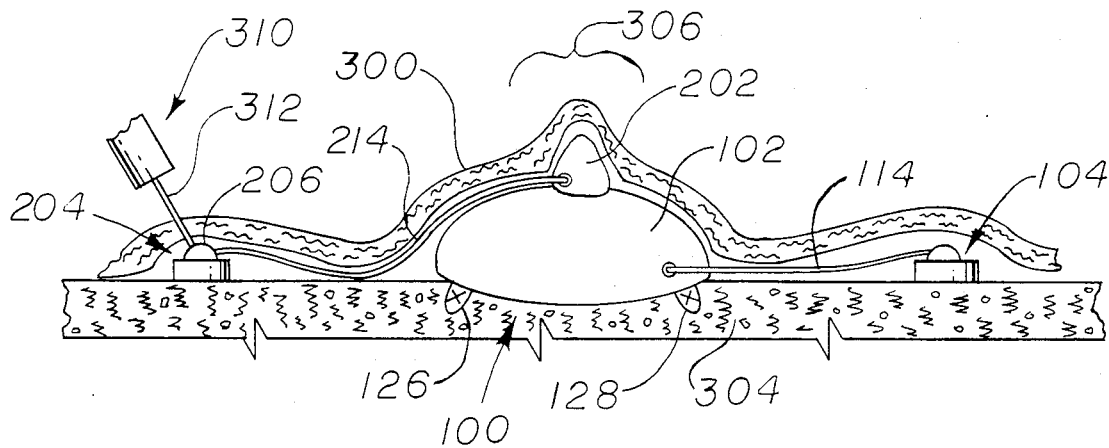
FIG. 5 is a partial sectional side view showing both envelopes of the tissue expander fully inflated.

Having described one embodiment of the tissue expander, the manner in which it can be used will now be described with reference to FIGS. 3-5. The tissue 300 in FIGS. 3-5 is shown in a somewhat exaggerated manner for purposes of clarity. It is to be understood that tissue 300 would rest directly upon expander 100 and buttons 104 and 204 when the expander 100 is implanted and would not be spaced away to the extent shown in FIGS. 3-5. In FIG. 3, a partial sectional side view of substantially uninflated dual envelope tissue expander 100 is shown implanted beneath the tissue 300 to be expanded (e.g., at the site where a female breast had been previously removed or a donor site on the patient's body) according to surgical procedures familiar to those skilled in the art of implantation of tissue expanders. Device 100 is placed in a surgically formed pocket beneath tissue 300 and sutures 302 are used to attach fixation tab 126 to an underlying body member 304 such as muscle tissue or fascia to hold envelope 102 and thus envelope 202 in a preselected orientation with respect to the tissue to be expanded. Sutures 303 are used to secure fixation tab 128 to member 304 and, in like manner, tabs 122 and 124 are fixed to member 304 to complete positioning and fixation of the device 100 beneath tissue 300. Envelope 202 is now positioned on the upper half of envelope 102 beneath tissue section 306 of tissue 300 which is to be expanded to a greater degree than the remainder of tissue 300 overlying envelope 102. Needle 312 of hypodermic syringe 310 is shown passing through tissue 300 and self-sealing dome 106 of injection button 104 to accomplish the gradual inflation of envelope 102 over an extended period of time. Envelope 102 is inflated with isotonic saline solution in a well known manner at such a rate that the tissue 300 is expanded over a reasonably short period of time (several days to several weeks), but not at such a rate that tissue necrosis occurs.

FIG. 4 shows envelope 102 fully inflated and shows that tissue 300 overlying the upper surface of envelope 102 has been expanded in size to substantially take the shape of envelope 102.

To achieve the advantages of the present invention, needle 312 is then introduced through tissue 300 and resealable dome 206 of injection button 204 as shown in FIG. 5. Envelope 202 is gradually inflated with isotonic saline over a period of time in the same manner as used for envelope 102 until envelope 202 is inflated to the degree desired by the surgeon to achieve an appropriately shaped tissue flap. As can be seen from FIG. 5 showing envelopes 102 and 202 as being fully inflated, tissue section 306 overlying inflated envelope 202 has been expanded to a greater extent than the remainder of the tissue 300 overlying inflated envelope 102 and this difference in expansion produces a skin flap with the desired shape. The tissue section 306 is expanded more than the remainder of the tissue 300 overlying the envelope 102 because the fixation tabs hold envelopes 102 and 202 in a fixed position beneath tissue 300.

Upon full inflation, device 100 is surgically removed and a prosthesis of a shape which is designed to utilize the shape of the expanded tissue is surgically implanted in its place or the tissue flap may be removed and surgically placed elsewhere on the body in accordance with well known techniques.

To achieve the best results, it is preferred that the envelope forming the base be inflated before the other envelopes situated on the upper half of the base envelope. Similar results may be achieved if both envelopes are gradually inflated at the same time.

FIG. 6 shows an alternative embodiment of the present invention as dual envelope tissue expander device 600 which consists essentially of a generally rectangular envelope 602 of biocompatible silicone elastomer which serves as a base envelope for device 600. A sheet of backing material 604 is fixed to and extends across the lower surface of envelope 602. A portion of material 604 extends beyond envelope 602 completely around envelope 602 to form a rim 606 which provides a means by which envelope 602 can be fixed to body members underlying the tissue to be expanded such as by suturing. Material 604 can be a polyester mesh-reinforced sheet of biocompatible silicone elastomer or can be a porous polyester felt of the type commonly used as porous ingrowth material for implantable prostheses. Envelope 602 contains an integral, self-sealing, injection button 608 of the type described in the aforementioned Bartolo patent which comprises a self-sealing injection port 610 which is composed of a laminate of layers of unidirectionally stretchable polyester fabric mesh and cured silicone elastomer which has been swollen in solvent to render the port 610 resealable after being punctured by a hypodermic needle. A raised palpation ring 612 of silicone elastomer surrounds the injection port 610 to enable the surgeon to feel the location of port 610 after implantation and a dome-shaped, metal needlestop 614 is secured to the back of button 608 to prevent accidental puncture of envelope 602 during inflation.

A second generally square envelope 622 of biocompatible silicone elastomer is fixed by means of a medical grade silicone adhesive to the upper side of envelope 602 directly opposite the side which is attached to material 604. Envelope 622 is placed closer to the right side of envelope 602 to expand tissue overlying that portion of device 600 to a greater extent than tissue overlying the left side of envelope 602 as viewed in FIG. 6. Envelope 622 contains an injection button 608' having an injection port 610', palpation ring 612' and needlestop 614' of the same type as was described for injection button 608.

In a further alternative embodiment, device 600 could be modified to place a third envelope of the type shown as 622 at the position occupied by button 608 in FIG. 6. A remote injection button means of the type shown as 104 with a tube such as that shown as 114 in FIG. 1 could be used to accomplish inflation of envelope 602.

In a further embodiment, it can be desirable to have the lower envelope forming the base of the tissue expander further contain a "shape retaining means". A shape retaining means can take the form of a rigid base which rests against underlying body members such as is taught in the aforementioned Radovan, et al. patent. Thus, one can use the Radovan, et al. teaching to provide expander 600 with a flat, rigid stainless steel base which could be encapsulated in a biocompatible silicone elastomer and affixed to the lower envelope 602 of expander 600 in place of backing material 604. Fixation tabs could be attached to the flat, rigid base or holes could be provided to permit the surgeon to suture the base and thus the device to underlying body members.

FIG. 7 shows another embodiment wherein expander 100 has been further modified to contain a shape retaining means in the form of two polyester mesh reinforced silicone elastomer sheets 700 and 702 which have been adhered to the upper and lower inside walls, respectively, of envelope 102 by means of a medical grade silicone adhesive. Equal lengths of polyester mesh reinforced silicone elastomer struts 704, 706, 708, 710 and 712 have been adhered to sheets 700 and 702. Other struts (not shown) would be situated opposite the struts shown in FIG. 7 along with several other such struts running along the center of sheets 700 and 702 to cause the envelope to be inflated in a flat shape when envelope 102 is inflated to its normal volume. This embodiment would provide a flat shaped lower envelope similar to the flat shaped envelope provided by envelope 602 of expander 600. The upper envelope 202 would then be inflated to expand the tissue overlying envelope 202.

Other modifications and variations in the multiple envelope tissue expander of the present invention will become apparent to those skilled in the art from an examination of the above specification and accompanying drawings. Therefore, other variations of the present invention may be made which fall within the scope of the appended claims even though such variations were not specifically discussed above.

That which is claimed is:

1. An implantable, multiple envelope tissue expander device for the controlled expansion of tissue consisting essentially of:
    (A) a first inflatable biocompatible envelope having a first inflation means associated therewith for the controlled inflation of said first envelope with a biocompatible fluid, said first envelope having a lower half to which a fixation means is attached and by which fixation means said first envelope is secured to an underlying body member beneath a section of tissue to be expanded to hold said first envelope in a preselected orientation with respect to the tissue to be expanded, and
    (B) a second inflatable, biocompatible envelope attached to the surface of that half of the first envelope which is opposite said underlying member, said second envelope having a second inflation means associated therewith, separate from said first inflation means, for the controlled inflation of said second envelope with a biocompatible fluid, said second envelope having a shape and a volume capacity which, upon appropriate inflation, is smaller in volume capacity than said first envelope and permits tissue overlying said second envelope to be expanded outwardly from said underlying body member to a greater extent than that tissue which overlies the remaining upper surface of said first envelope to thereby cause the overlying tissue to substantially assume the shape of the upper surfaces of the fully inflated envelopes.

2. The tissue expander device as claimed in claim 1 wherein said envelopes are made of a biocompatible silicone elastomer.

3. The tissue expander device as claimed in claim 1 wherein said first envelope contains a shape retaining means.

4. The tissue expander device as claimed in claim 1 wherein the volume capacity of said second envelope is no greater than 50% of the volume capacity of said first envelope.

5. The tissue expander device as claimed in claim 4 wherein said first envelope contains a shape retaining means.

6. A method of expanding tissue to form an area of tissue having a preselected shape which comprises the steps of
    (I) implanting beneath a section of tissue to be expanded a multiple envelope tissue expander device consisting essentially of (A) a first inflatable biocompatible envelope having a first inflation means associated therewith for the controlled inflation of said first envelope with a biocompatible fluid, said first envelope having a lower half to which a fixation means is attached and by which means said first envelope is secured to an underlying body member beneath the tissue to be expanded to hold said first envelope in a preselected orientation with respect to the tissue to be expanded, and (B) a second inflatable, biocompatible envelope which is attached to the surface of that half of the first envelope which is opposite said underlying member, said second envelope having a second inflation means associated therewith, separate from said first inflation means, for the controlled inflation of said second envelope with a biocompatible fluid, said second envelope having a shape and a volume capacity which, upon appropriate inflation, is smaller in volume capacity than said first envelope and permits tissue overlying said second envelope to be expanded outwardly from said underlying body member to a greater extent than that tissue which overlies the remaining upper surface of said first envelope to thereby cause the overlying tissue to assume the approximate shape of the upper surfaces of the fully inflated envelopes,
    (II) securing said fixation means to said underlying body member to hold said envelopes in a preselected orientation with respect to the tissue to be expanded,
    (III) inflating said first envelope gradually over a period of time to expand the tissue overlying said first envelope,
    (IV) inflating said second envelope gradually over a period of time to expand the tissue overlying said second envelope to a greater extent than is accomplished by the inflation of said first envelope, and
    (V) removing said expander.

7. The method as claimed in claim 6 wherein step (III) is performed at the same time as step (IV).

8. The method as claimed in claim 6 wherein said first envelope contains a shape retaining means.

9. The method as claimed in claim 6 wherein the volume capacity of said second envelope is no greater than 50% of the volume capacity of the first envelope.

10. The method as claimed in claim 9 wherein said first envelope contains a shape retaining means.

11. The method as claimed in claim 6 wherein step (III) is performed prior to commencement of step (IV).

12. The method as claimed in claim 11 wherein the volume capacity of said second envelope is no greater than 50% of the volume capacity of the first envelope.

13. The method as claimed in claim 12 wherein said first envelope contains a shape retaining means.

14. The method as claimed in claim 6 wherein said envelopes are made of a biocompatible silicone elastomer.

15. The method as claimed in claim 14 wherein the volume capacity of said second envelope is no greater than 50% of the volume capacity of the first envelope.

16. The method as claimed in claim 15 wherein said first envelope contains a shape retaining means.

* * * * *